Figure 1:
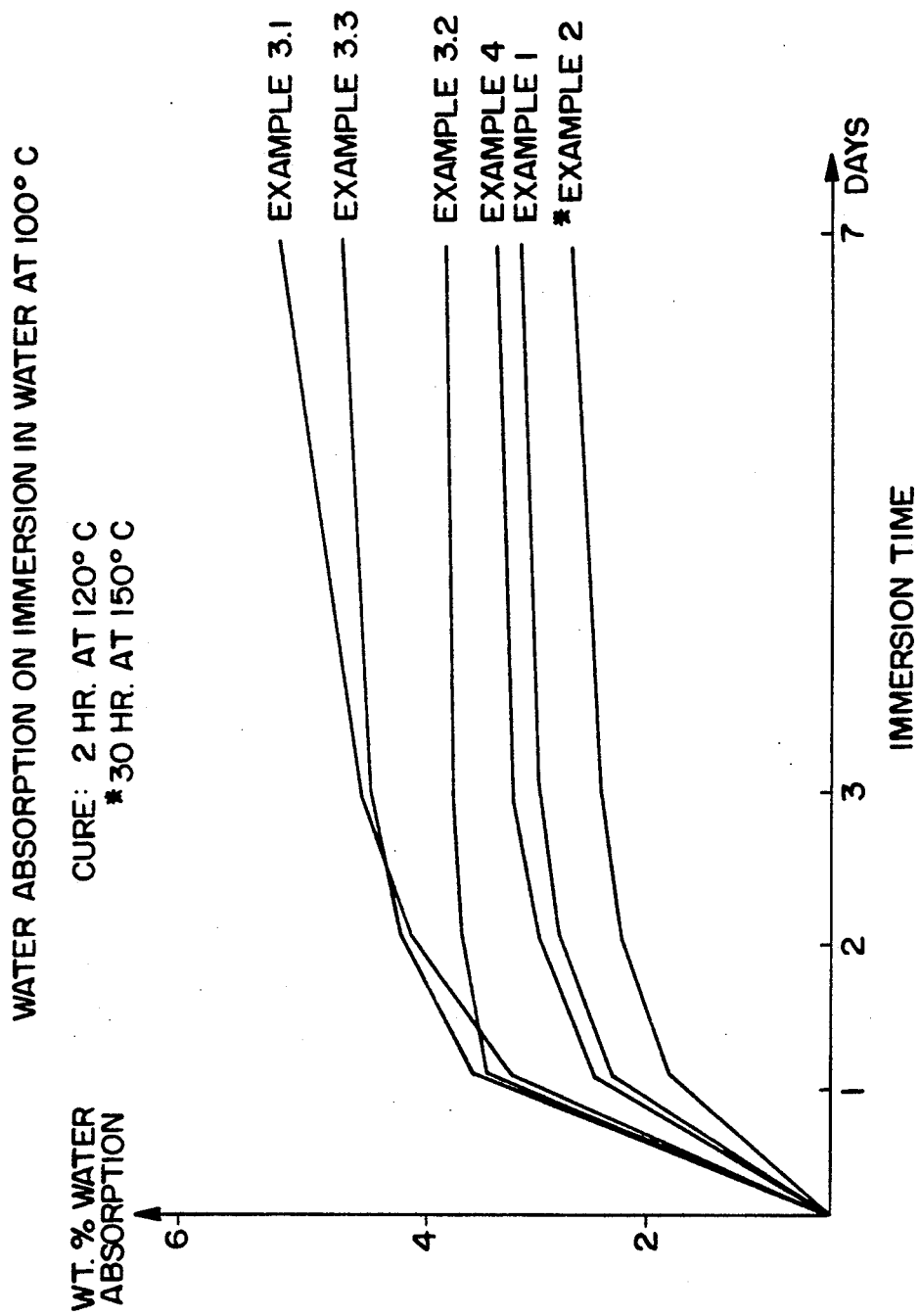

United States Patent [19]

Burba et al.

[11] Patent Number: 5,080,740

[45] Date of Patent: Jan. 14, 1992

[54] PROCESS FOR THE FABRICATION OF FIBER-REINFORCED WOUND STRUCTURES FROM EPOXY RESINS AND 3-(1-(2'-AMINOETHYL)-1,3-DIAZA-2-CYCLOPENTEN-2-YL)HEPTANE AND/OR (1-(2'-AMINOETHYL)-1,3-DIAZA-2-CYCLOPENTEN-2-YL)-2,4,4-TRIMETHYL-1-PENTANE

[75] Inventors: Christian Burba, Herbern; Herbert Franz, Hamm; Alwin Krotzek, Werne; Werner Mrotzek, Dortmund, all of Fed. Rep. of Germany

[73] Assignee: Schering AG, Bergkamen, Fed. Rep. of Germany

[21] Appl. No.: 447,646

[22] Filed: Dec. 8, 1989

[30] Foreign Application Priority Data

Dec. 27, 1988 [DE] Fed. Rep. of Germany ....... 3843986

[51] Int. Cl.$^5$ .............................................. B32B 31/00
[52] U.S. Cl. .................................... 156/172; 156/187; 156/192; 156/330; 242/7.02; 242/7.22; 285/150; 525/523; 528/94

[58] Field of Search .......................... 525/523; 528/94; 156/192, 330, 172, 187; 285/150; 242/7.02, 7.22

[56] References Cited

U.S. PATENT DOCUMENTS

| 4,076,869 | 2/1978 | Flynn | 156/330 |
| 4,504,086 | 3/1985 | Carrow | 156/172 |

FOREIGN PATENT DOCUMENTS

| 51-17299 | 2/1976 | Japan | 528/94 |
| 57-71154 | 5/1982 | Japan | 528/94 |

*Primary Examiner*—John J. Gallagher

[57] ABSTRACT

The invention relates to a process for the fabrication of fiber-reinforced wound structures, and particularly pipe fittings, by impregnation of heat-resistant fibers with binders based on epoxy resins and 3-[1-(2'-aminoethyl)-1,3-diaza-2-cyclopenten-2-yl]-heptane and/or [1-(2'-aminoethyl)-1,3-diaza-2-cyclopenten-2-yl]-2,4,4-trimethyl-1-pentane as curing agent and commonly used fillers, pigments, dyes, accelerators, curing agents, wetting and flow-control agents, and reactive diluents.

9 Claims, 2 Drawing Sheets

PROCESS FOR THE FABRICATION OF FIBER-REINFORCED WOUND STRUCTURES FROM EPOXY RESINS AND 3-(1-(2'-AMINOETHYL)-1,3-DIAZA-2-CYCLOPENTEN-2-YL)HEPTANE AND/OR (1-(2'-AMINOETHYL)-1,3-DIAZA-2-CYCLOPENTEN-2-YL)-2,4,4-TRIMETHYL-1-PENTANE

The invention relates to a process for the fabrication of fiber-reinforced wound structures, and particularly pipe fittings, by impregnation of heat-resistant fibers with binders based on epoxy resins which on the average contain more than one epoxy group per molecule, and amine curing agents for the epoxy resins, along with auxiliary and additive substances, by conventional methods, which is characterized in that the binders used are curable mixtures composed of (A) at least one liquid epoxy resin having epoxy values of from 0.4 to 0.6;

3-[1-(2'aminoethyl)-l,3-diaza-2-cyclopenten-2-yl]heptane and/or [1-(2'-aminoethyl)-1,3-diaza-2-cyclopenten-2-yl]-2,4,4-trimethyl-1-pentane; and (C) commonly used fillers, pigments, dyes, accelerators, curing agents, wetting and flow-control agents, and reactive diluents.

In industry, metal tanks and pipelines are still used predominantly in many areas. In use, some of the typical properties of metals manifest themselves in a negative way, particularly where aqueous or other corrosive media are used or where light weight is desirable.

Moreover, because of the good thermal conductivity of metals, such tanks and pipes have to be insulated at great expense wherever a temperature other than ambient temperature is the operating temperature.

To compensate for these drawbacks by appropriate measures, enormous amounts of money have to be expended every year.

This is why a concerted effort has been under way for some time to utilize in this field the favorable properties of fiber-reinforced resins, such as low weight, good resistance to chemicals and in some cases also to solvents, adaptability with respect to constructional requirements, economy of manufacture as compared with other corrosion-resistant materials of construction, such as glass, metal or porcelain enamel, low maintenance and repair costs.

The manufacture of tanks and pipe from fiber-reinforced resins is done by the filament-winding method and largely by machine. However, present-day fabricating techniques permit only the manufacture of relatively simple geometric shapes. Allowance has to be made for filling and reclaiming lines of tanks, for branches of pipelines, and for the fabrication of pipe fittings, and these have to be fabricated manually.

At the present state of the art, the corresponding prefabricated elements are laminated onto the respective structures at the appropriate points.

The junctions are weak spots which call for special measures. To achieve the mechanical strength which the application requires, the fibrous material must be increased disproportionately in these areas, which imposes a number of special requirements on the binder, including good wetting properties for the fibers and fabrics, with practical viscosities and relatively long pot lives.

Good wetting properties are essential since with the requisite high proportion of fibers at the junctions assurance must be provided for the complete saturation of the entire area, including overlaps, to preclude a drop in the mechanical values. At the same time, the viscosity must be adjusted so that during the laminating operation no binder is squeezed out and the binder remains uniformly dispersed in the fabric also before or during the cure. In other words, the binder should not build up on one side under gravitational force; much less should it ooze out.

Since fabrication is manual and therefore slow, the pot life must be sufficiently long. This requirement cannot be circumvented by reducing the batch size as in the case of large structures large amounts of binder are needed.

Premature gelation is undesired if the cured products are to possess uniform and reproducible physical and mechanical end values. Thus, during fabrication in the shop or during repairs in the field, gelation should not set in before the work has been completed. Care should be taken to assure that the binder is usable over a temperature range appropriate to the season.

The resistance to chemicals of fiber-reinforced resins based on epoxy resins is well known.

However, in the transmission of water, and particularly of hot water or steam of up to 120° C., a lowering of the level of thermal properties, as determined by the torsion pendulum test (DIN 53,445), for example, has been observable even after a relatively short time.

This lowering of the level of thermal properties has in some cases so adverse an effect on the structural properties of fiber-reinforced composite materials that they cannot be employed in the aforesaid applications.

Of the great many available curing agents, only 1-amino-3,3,5-trimethyl-5-aminomethylcyclohexane (isophorone diamine) has so far proved to possess the requisite physical properties.

However, isophorone diamine is a relatively expensive curing agent. Besides, it is not always available in sufficient quantities and also has a few processing drawbacks. These include, in particular, a short processing time, a high cure temperature, and physiological problems.

Many attempts have therefore been made in the past to develop alternative curing agents which result in properties in the cured resins that are comparable to those produced by isophorone diamine.

While the imidazolines based on reaction products of straight-chain monomeric fatty acids having from 2 to 18 carbon atoms, and more particularly from 2 to 5 carbon atoms, which have been proposed up to now have proved to be physiologically safe, they are not sufficiently resistant to hot water, as evidenced by the pronounced drop in the heat-distortion temperature (HDT) after immersion in boiling water.

Figure 2:
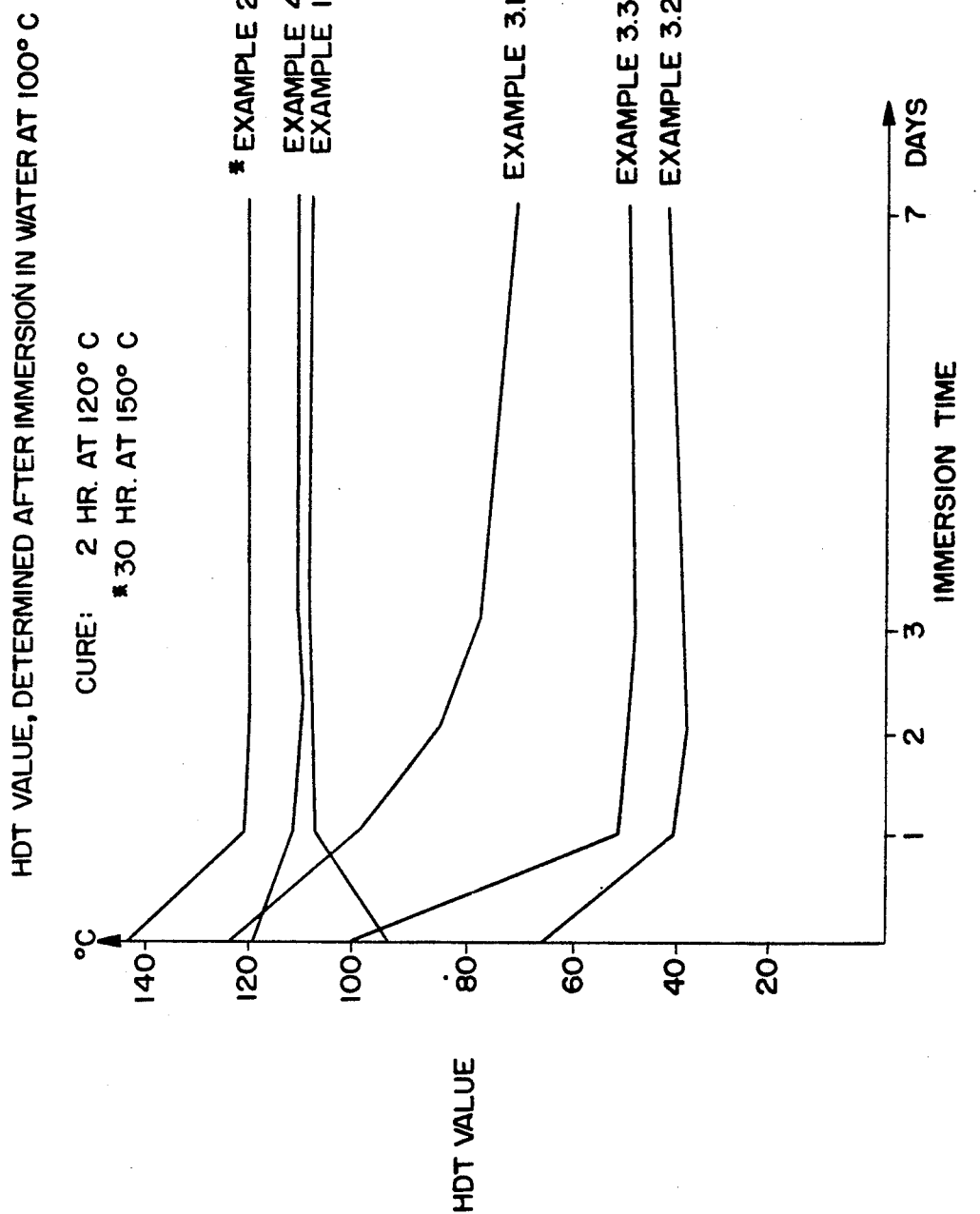

Empirical values have shown that not only the imidazolines from short-chain monocarboxylic acids but, surprisingly, also the imidazolines from the hydrophobic long-chain monomeric and even from the branched-chain dimeric fatty acids are capable of absorbing rather large amounts of water, with a corresponding drop in the HDT values. This has not been the case with cycloaliphatic diamines such as isophorone diamine. (See FIGS. 1 and 2.)

It has therefore been generally held that imidazolines based on fatty acids are unsuited for use as curing agents for epoxy resins when the end products are to be subjected to loading with water.

Surprisingly, it has now been found that 3-[1(2'-aminoethyl)-1,3-diaza-2-cyclopenten-2-yl]heptane and/or [1-(2'-aminoethyl)-1,3-diaza-2-cyclopenten-2-yl]-2,4,4-trimethyl-1-pentane imparts to cured epoxy resins based on bisphenol A and bisphenol F resistance to long-time exposure to hot water or superheated steam of up to 120° C. In addition, it improves their processing properties and, in particular, extends their pot life to practical lengths of time which permit also the manual fabrication of large workpieces.

The invention thus has as its object a process for the fabrication of fiber-reinforced wound structures, and particularly pipe fittings, by impregnation of heat-resistant fibers with binders based on epoxy resins which on the average contain more than one epoxy group per molecule, and amine curing agents for the epoxy resins, along with auxiliary and additive substances, by conventional methods, which is characterized in that the binders used are curable mixtures composed of (A) at least one liquid epoxy resin having epoxy values of from 0.4 to 0.6;

(B) 3-[1-(2'-aminoethyl)-1,3-diaza-2-cyclopenten-2-yl]heptane and/or [1-(2'-aminoethyl)-1,3-diaza-2-cyclopenten-2-yl]-2,4,4-trimethyl-1-pentane; and (C) commonly used fillers, pigments, dyes, accelerators, curing agents, wetting and flow-control agents, and reactive diluents.

A further object of the invention is a process characterized in that bisphenol A and/or bisphenol F having epoxy values of between 0.45 and 0.55 are used as liquid epoxy resin according to (A).

The epoxy resins used in accordance with the invention are glycidyl ethers with two or more epoxy groups per molecule, and preferably glycidyl ethers based on mono- or polyhydric phenols. In accordance with the invention, glycidyl ethers of 2,2-bis(4-hydroxyphenyl)-propane (bisphenol A) having epoxy values of from 0.4 to 0.6, and particularly the compounds which have epoxy values of from 0.45 to 0.55 and are liquid at room temperature, are preferred. The glycidyl ethers based on bisphenol F and the novolacs have also proved advantageous.

3-[1-(2'Aminoethyl)-1,3-diaza-2-cyclopenten-2-yl]heptane is prepared by reacting 2-ethylhexoic acid with diethylenetriamine in a molar ratio of at least 1:1. [1-(2'Aminoethyl)-1,3-diaza-2-cyclopenten-2-yl]-2,4,4-trimet 3,5,5-trimethylhexoic acid with diethylenetriamine in a molar ratio of at least 1:1. As a rule, they are used in amounts of from 10 to 20 parts by weight, and preferably from 12 to 18 parts by weight, and more particularly of 15 parts by weight, per 100 parts by weight of epoxy resin.

To modify the processing and curing properties, the generally known modifiers commonly employed in this field, such as customary fillers and/or stiffeners, pigments, dyes, accelerators, wetting and flow-control agents, reactive diluents, and curing agents may also be used, if desired. As reinforcements, the commonly used glass fibers are preferably employed.

Among the glycidyl ethers which in accordance with the invention are also used, those based on alicyclic alcohols, such as 1,4-dimethylolcyclohexane, and aliphatic alcohols, especially dihydric or trihydric alcohols having from 4 to 8 carbon atoms, such as butanediols, hexanediols, octanediols or glycerol, which may be lengthened by the addition of ethylene oxide or propylene oxide, are preferred.

The amount of the reactive diluents usually ranges from 5 to 10, and preferably from 6 to 8, percent by weight, based on the epoxy resin according to (A).

Suitable for use as commonly used curing agents are, in particular, cycloaliphatic amines such as isophorone diamine, 1,2-diaminocyclohexane, 4,4'-diamino-3,3'-dimethyldicyclohexylmethane, 1,7-bis-[1-(2'-aminoethyl)-1,3-diaza-2-cyclopenten-2-yl)-heptane or 1,8-bis-[1-(2'-aminoethyl)-1,3-diaza-2-cyclopenten-2-yl]-octane.

DESCRIPTION OF THE LAMINATING OPERATION

The fabrication of a pipe section branching off (whether at right angles or not) from a larger-diameter main pipe is carried out by the use of pipe sections prefabricated by machine, as mentioned earlier. In a first step, an opening corresponding to the diameter of the branch pipe is cut into the cured main pipe. In a second step, one end of the branch pipe, which has also been cured, is cut at the angle at which it is to branch off. And in a third step, the two pipes are laminated onto each other by conventional methods. To this end, they are first fixed in position relative to each other by means of a jig, and a laminate is then built up manually by the wet-layup technique over the area where they are joined. Specifically, the two pipe sections are contacted to form a joint therebetween, and the joint is overwound or overwrapped with heat resistant fibers which have been impregnated with the aforementioned epoxy resin binder at a processing temperature.

For a bubble-free laminate build-up and adequate strength of the pipe joint, it is essential that the materials used to make the joint be optimally wetted by the resin system and that the latter adhere well to the surfaces of the pipe sections being joined.

The optimum wetting properties required call for the use of a laminating system which has very low viscosity even at room temperature since the manual operation does not permit the system to be heated for adjustment of the viscosity. Moreover, the material should not gel already during the laminating operation as this could significantly reduce the adhesion of the individual layers of the laminate to one another. Besides, a long gel time of the system will considerably facilitate the fabrication process since only one batch of materials can be employed even when the joint covers a large area, the likelihood of faulty mixing and proportioning thus being minimized.

On completion of the build-up of the laminate, the joint is heat-cured. However, curing should be done at the lowest possible temperature to keep the thermal stresses in the structure to a minimum, and also to be able to carry out curing on the site, if necessary.

For a good level of properties of the overall structure, the properties of the joint should match those of the joined pipe sections so that no peak stresses build up in the structure due to the material. Since the use of the same fibrous material as reinforcing material for pipe sections and joint usually poses no difficulties, this requirement will be met whenever comparable properties are achieved so far a the matrix is concerned.

EXAMPLE 1

38.88 kg of 2-ethylhexoic acid, 27.81 kg of diethylenetriamine and 0.34 kg of para-toluenesulfonic acid are charged under nitrogen. The mixture is heated to about 160–170° C. with stirring. At that temperature, condensation sets in. The temperature is then gradually increased to a maximum of 280° C., an amine condenser being used to assure that only water, and not diethylenetriamine, distills off. Vacuum is then gradually applied up to about 800 millibars.

The reaction mixture is held at 280° C. and about 800 millibars until the calculated amount of condensate is reached and the imidazoline content exceeds 80%, as determined by infrared spectroscopy.

The filtered product has the following characteristics:

| Amine value: | Approx. 450 |
|---|---|
| Viscosity: | Approx. 500 mPa · s/25° C. |
| Imidazoline content: | Approx. 80% |

EXAMPLE 2

Commercial isophorone diamine.

| Amine value: | 660 |
|---|---|
| Viscosity: | 15 mPa · s/25° C. |

EXAMPLE 3

7 Same as Example 1, except that in place of 2-ethylhexoic acid an equivalent amount of propionic acid (3.1), tall oil fatty acid (3.2) and dimeric fatty acid (dimeric proportion, 96%) (3.3), respectively, are used. The product has the following characteristics:

| 3.1 | Amine value: | 700 |
|---|---|---|
|  | Viscosity: | 20 mPa · s/25° C. |
|  | Imidazoline content: | 80% |
| 3.2 | Amine value: | 260 |
|  | Viscosity: | 200 mPa · s/25° C. |
|  | Imidazoline content: | 91% |
| 3.3 | Amine value: | 300 |
|  | Viscosity: | 5000 mPa · s/25° C. |

EXAMPLE 4

Imidazoline from 3.3.5-trimethylhexoic acid (isononanoic acid) and diethylenetriamine.

316 g of isononanoic acid, 206 g of diethylenetriamine and 0.5 g of para-toluenesulfonic acid are charged under nitrogen. The mixture is heated to about 160–170° C. with stirring. At that temperature, condensation sets in. The temperature is then gradually increased to a maximum of 260° C., an amine condenser being used to assure that only water, and not diethylenetriamine, distills off. Since the theoretical quantity of water does not distill off under these conditions, vacuum is gradually applied up to about 100 millibars.

The reaction mixture is held at 260° C. and about 100 millibars until the calculated amount of condensate is reached and the imidazoline content exceeds 80%, as determined by infrared spectroscopy.

The filtered product has the following characteristics:

| Amine value: | 437 |
|---|---|
| Viscosity: | 105 mPa · s/25° C. |
| Imidazoline content: | 88% |

TEST PROCEDURE

For determination of the level of mechanical properties, 15 parts by weight of the product described in Examples 1, 3 and 4 and 25 parts by weight of the product described in Example 2 were mixed with 100 parts by weight of a low-viscosity epoxy resin based on bisphenol A (epoxy value, 0.54) and cured in a steel mold for 2 hours at 120° C. to give flat molded parts 4 mm thick.

From these parts, test specimens were then cut by sawing or milling, and on these the property values given in Table 1 which follows were determined in keeping with the respective test specifications.

The dimensions of the test specimens used in the various tests were as follows:

Three-point flexural test: 80×10×4 mm
Tensile test: Gage length No. 3 in conformity with DIN 53,455
Heat-distortion test: 120×10×4 mm

TABLE 1

Properties of various binder systems after curing for 2 hours at 120° C.

| Property | Unit | Example 1 | Example 2 | Example 3.1 | Example 4 |
|---|---|---|---|---|---|
| Tecam gel time for 250 g at 23° C. | Minute | 1200 | 115 | 400 | 760 |
| Flexural strength (DIN 53,452) | N/mm² | 102 | 102 | 110 | 60 |
| Tensile strength (DIN 53,455) | N/mm² | 67 | 45.3 | 75 | 65 |
| Elongation (DIN 53,455) | % | 3.1 | 1.9 | 3.5 | 3.5 |
| Heat-distortion temperature (DIN 53,461) | °C. | 108 | 123 | 120 | 123 |
| Transition temperature (DIN 53,445) | °C. | 145 | 158 | 145 | 157 |

TABLE 2

HDT values of various binder systems after immersion in boiling water

| | Immersion time in boiling water | | | | |
|---|---|---|---|---|---|
| | 0 value | 1 day | 2 days | 3 days | 7 days |
| Example 1 | 108 | 108 | 108 | 109 | 109 |
| Example 2 | 123 | 118 | 118 | 117 | 117 |
| Example 3.1 | 120 | 99 | 84 | 77 | 70 |
| Example 4 | 123 | 111 | 110 | 110 | 111 |

We claim:

1. A process for the fabrication of fiber-reinforced wound structures, which comprises contacting two pipe sections for form a joint therebetween, and overwinding or overwrapping the joint with heat-resistant fibers impregnated at a processing temperature with (i) a binder based on epoxy resins which on the average contain more than one epoxy group per molecule, (ii) an amine curing agent for the epoxy resins, and (iii) auxiliary and additive substances, wherein the binder contains at least one liquid epoxy resin having an epoxy value of from 0.4 to 0.6 and the curing agent is 3-[1-(2'-aminoethyl)-1,3-diaza-2-cyclopenten-2-yl]heptane or [1-(2'-aminoethyl)-1,3-diaza-2-cyclopenten-2-yl]-2,4,4-trimethyl-1-pentane or mixtures thereof.

2. A process as defined in claim 1, wherein the auxiliary and additive substances are selected from the group consisting of a filler, pigment, dye, accelerator, curing agent, wetting agent, flow-central agent and reactive diluent or mixtures thereof.

3. A process as defined in claim 1, wherein the liquid epoxy resin is bisphenol A or bisphenol F or mixtures thereof having an epoxy value of between 0.45 and 0.55.

4. A process as defined in claim 11, wherein the binder based on epoxy resins and the amine curing agent for the epoxy resins is liquid at the processing temperature.

5. A process as defined in claim 1, wherein the 3-[1-(2'-aminoethyl)-1,3-diaza-2-cyclopenten-2-yl]heptane or [1-(2'-aminoethyl)-1,3-diaza-2-cyclopenten-2-yl]2,4,4-trimethyl-1-pentane or mixtures thereof are used in an amount of from 10 to 20 parts by weight per 100 parts by weight of liquid epoxy resin.

6. A process as defined in claim 2, wherein the auxiliary and additive substances include a reactive diluent which is a glycidyl ether based on aliphatic or alicyclic polyols having from 4 to 8 carbon atoms.

7. A process as defined in claim 2, wherein the auxiliary and additive substances include a curing agent which is a cycloaliphatic amine.

8. A process as defined in claim 3, wherein the binder based on epoxy resins and the amine curing agent for the epoxy resins is liquid at the processing temperature.

9. A process as defined in claim 1, wherein the liquid epoxy resin is a novolac resin having an epoxy value of from 0.4 to 0.6.

* * * * *